US 7,914,751 B2

(12) United States Patent
Oertmann

(10) Patent No.: US 7,914,751 B2
(45) Date of Patent: Mar. 29, 2011

(54) STERILE CONTAINER

(75) Inventor: Friedrich-Wilhelm Oertmann, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 1060 days.

(21) Appl. No.: 11/543,463

(22) Filed: Oct. 3, 2006

(65) Prior Publication Data

US 2007/0062830 A1 Mar. 22, 2007

Related U.S. Application Data

(63) Continuation of application No. PCT/EP2005/003843, filed on Apr. 12, 2005.

(30) Foreign Application Priority Data

Apr. 16, 2004 (DE) .......................... 10 2004 020 804

(51) Int. Cl.
*A61L 2/00* (2006.01)
*A61L 9/00* (2006.01)
(52) U.S. Cl. .......................... 422/297; 422/292; 422/295
(58) Field of Classification Search .................... 210/97, 210/445; 422/297
See application file for complete search history.

(56) References Cited

U.S. PATENT DOCUMENTS

| | | |
|---|---|---|
| 4,105,407 A | 8/1978 | Sanderson |
| 4,149,650 A | 4/1979 | Whelchel et al. |
| 4,196,166 A | 4/1980 | Sanderson et al. |
| 4,228,914 A | 10/1980 | Sanderson |
| 4,247,517 A | 1/1981 | Sanderson et al. |

(Continued)

FOREIGN PATENT DOCUMENTS

DE 26 51 291 6/1977

(Continued)

OTHER PUBLICATIONS

Storz, W. et al., *Martin Medizin Technik Designs New Container with "MicroStop" Sterile Barrier*, Zentralsterilisation, vol. 9, 2001, pp. 446-453, (pp. 446-449 in the German language, pp. 450-453 in the English language).

*Primary Examiner* — Sean E Conley
*Assistant Examiner* — Regina Yoo
(74) *Attorney, Agent, or Firm* — Lipsitz & McAllister, LLC

(57) ABSTRACT

To improve a sterile container, in particular, for receiving and storing surgical instruments or surgical material under sterile conditions, comprising a receiving space formed by a container bottom and container walls, a lid for closing the receiving space, a sterile barrier permanently defining a sterile flow path for establishing a fluid connection between the receiving space and an environment outside of the sterile container, and an overpressure flow path defining a fluid connection between the receiving space and the environment outside of the sterile container, wherein the overpressure flow path is closed when the sterile container is in a sterile position in which an exchange of gas between the receiving space and the environment outside of the sterile container is only possible through the sterile flow path, and wherein the overpressure flow path is at least partially open when the sterile container is in an overpressure position in which a pressure difference between pressures prevailing in the receiving space and in the environment outside of the sterile container exceeds a minimum pressure difference, so that design and maintenance of the sterile container are particularly simple, it is proposed that a gas flow cross section of the sterile flow path be alterable for formation of the overpressure flow path.

32 Claims, 4 Drawing Sheets

U.S. PATENT DOCUMENTS

| | | | |
|---|---|---|---|
| 4,251,482 A | 2/1981 | Sanderson et al. | |
| 4,349,118 A | 9/1982 | Sanderson et al. | |
| 4,374,570 A | 2/1983 | Sanderson et al. | |
| 4,416,417 A | 11/1983 | Sanderson et al. | |
| 4,512,498 A | 4/1985 | Leibinger | |
| 4,551,311 A | 11/1985 | Lorenz | |
| 4,671,943 A * | 6/1987 | Wahlquist | 422/300 |
| 5,019,345 A | 5/1991 | Lorenz | |
| 5,176,884 A | 1/1993 | Taschner et al. | |
| 5,352,416 A * | 10/1994 | Wagner | 422/108 |
| 6,041,794 A | 3/2000 | Lin et al. | |
| 6,620,390 B1 * | 9/2003 | Wagner | 422/297 |
| 6,994,128 B2 | 2/2006 | Gleichauf et al. | |
| 2004/0256268 A1 | 12/2004 | Gleichauf et al. | |
| 2004/0256269 A1 * | 12/2004 | Gleichauf et al. | 206/439 |
| 2004/0256270 A1 | 12/2004 | Gleichauf et al. | |
| 2005/0045551 A1 | 3/2005 | Jakab et al. | |
| 2006/0076081 A1 | 4/2006 | Gleichauf et al. | |

FOREIGN PATENT DOCUMENTS

| | | | |
|---|---|---|---|
| DE | 31 46 349 | | 6/1983 |
| DE | 35 00 026 | | 7/1986 |
| DE | 297 20 450 | | 2/1998 |
| DE | 199 34 176 | | 2/2000 |
| DE | 102 10 905 | | 7/2003 |
| GB | 1074275 | | 7/1967 |
| WO | 81/02108 | | 8/1981 |
| WO | 92/07588 | | 5/1992 |
| WO | WO 03/041604 | * | 5/2003 |
| WO | WO 03/041749 | * | 5/2003 |

* cited by examiner

STERILE CONTAINER

This application is a continuation of international application number PCT/EP2005/003843 filed on Apr. 2, 2005.

The present disclosure relates to the subject matter disclosed in international application number PCT/EP2005/003843 of Apr. 12, 2005 and German application number 10 2004 020 804.2 of Apr. 16, 2004, which are incorporated herein by reference in their entirety and for all purposes.

BACKGROUND OF THE INVENTION

The invention relates to a sterile container, in particular, for receiving and storing surgical instruments or surgical material under sterile conditions, comprising a receiving space formed by a container bottom and container walls, a lid for closing the receiving space, a sterile barrier permanently defining a sterile flow path for establishing a fluid connection between the receiving space and an environment outside of the sterile container, and an overpressure flow path defining a fluid connection between the receiving space and the environment outside of the sterile container, wherein the overpressure flow path is closed when the sterile container is in a sterile position in which an exchange of gas between the receiving space and the environment outside of the sterile container is only possible through the sterile flow path, and wherein the overpressure flow path is at least partially open when the sterile container is in an overpressure position in which a pressure difference between pressures prevailing in the receiving space and in the environment outside of the sterile container exceeds a minimum pressure difference. Sterile containers of the kind described at the outset with sterile barriers are used to enable exchange of fluid, i. e., exchange of gases, liquids or gas-liquid mixtures, for example, air, in particular, during storage of the sterile container, between the environment outside of the sterile container and the receiving space. During sterilization of the sterile container, large pressure differences between the environment outside of and the receiving space inside of the sterile container may arise and cause damage to the sterile container by, for example, the sterile container being compressed or inflated by pressure forces acting thereon. To avoid damage, when a minimum pressure difference is exceeded, additional bypass flow paths are opened, which permit a high air mass exchange within a short time, which would not be possible via the sterile flow path. As sterile barriers, there are known, on the one hand, filters made of porous material, through which germs and bacteria are unable to pass, and, on the other hand, specially shaped flow paths, which do allow free passage of air, which, in principle, would also permit bacteria and germs to penetrate into the interior of the container, but the aerodynamic conditions in these special flow paths are configured such that there are areas where no flow occurs. Bacteria and germs settle in these flow-free areas and, therefore, cannot enter the receiving space of the sterile container.

In principle, it would be possible to provide a pressure relief valve on the sterile container, which, in the event the minimum pressure difference is exceeded, permits exchange of gas between the environment outside of and the receiving space inside of the sterile container. For this purpose, a further opening would, however, have to be provided in the sterile container, and, in addition, such a pressure relief valve would have to be serviced at regular intervals.

The object of the present invention is, therefore, to so improve a sterile container of the kind described at the outset that design and maintenance of the sterile container are particularly simple.

SUMMARY OF THE INVENTION

This object is accomplished, in accordance with the invention, in a sterile container of the kind described at the outset in that a gas flow cross section of the sterile flow path is alterable for formation of the overpressure flow path.

Accordingly, a sterile flow path that is unalterable in its configuration is not provided, but rather a sterile flow path that has a variable flow cross section. When a minimum pressure difference between pressures prevailing in the environment outside of and in the receiving space inside of the sterile container is exceeded, it is then possible, in a sterile container according to the invention, to alter, in particular, to increase, the gas flow cross section of the sterile flow path, so as to open up a bypass flow path for a gas exchange that is required to relieve the prevailing pressure difference. An overpressure flow path is thus formed by altering the gas flow cross section of the sterile flow path. In doing so, the sterile flow path could be separate from the overpressure flow path or in fluid communication therewith.

It is advantageous for the sterile flow path to have a first flow cross section in the sterile position, for the sterile flow path to have a second flow cross section in the overpressure position, and for the overpressure flow path to have a third flow cross section, which corresponds to the difference between the first flow cross section and the second flow cross section. In pure mathematical terms, this means that the overpressure flow path is obtained from a difference between two different flow cross sections of the sterile flow path.

In particular, this is the case when the sterile flow path and the overpressure flow path are in fluid communication with one another or the overpressure flow path forms part of the increasing sterile flow path. In particular, in the last-mentioned case, the design of the sterile container is significantly simplified because no additional openings need be provided on the sterile container.

The sterile barrier is particularly well protected against outside influences when it is arranged on an inner side of the sterile container.

A holding device is preferably provided for holding at least one part of the sterile barrier on the sterile container. This makes it possible to arrange the sterile barrier in a simple way on the sterile container, for example, to mount it thereon or connect it thereto.

In accordance with a preferred embodiment of the invention, it may be provided that at least one part of the sterile barrier and the holding device are releasably connectable, and that the at least one part of the sterile barrier is releasable from the holding device in a remove position and is held on the holding device in a connect position. This allows at least one part of the sterile barrier to be released from the sterile container for cleaning purposes.

Advantageously, the sterile barrier is constructed in the form of a Pasteurian loop (tortuous path), and the sterile flow path is of meander-shaped configuration. No consumables are needed for this kind of sterile barrier, on the contrary, a Pasteurian loop (tortuous path) can be cleaned in a simple way, sterilized and reused virtually as often as required.

It is advantageous for the Pasteurian loop (tortuous path) to comprise a first carrier and a second carrier facing the first carrier, for the first carrier and the second carrier to each carry concentric ring-shaped projections extending in the direction towards the respective other carrier, and for a ring-shaped projection of the one carrier to respectively enter at least partially in between two ring-shaped projections of the other carrier in the sterile position. Owing to this configuration, a meander-shaped flow path is formed, i. e., no straight-lined connection through the sterile barrier exists, so that no straight-lined flow along the sterile flow path can be formed in the sterile position. Gas and particles, for example, germs and bacteria, contained therein are subjected to successive changes in direction while flowing through the sterile flow path, and heavier particles collect in flow-free areas of the flow path.

A particularly simple configuration of the sterile flow path is obtained when the ring-shaped projections of the one carrier have a wall thickness which is smaller than a spacing between adjacent ring-shaped projections of the other carrier.

The ring-shaped projections of the two carriers advantageously have a height which is smaller than a spacing of the two carriers from one another in the sterile position. It is thereby ensured that the sterile flow path is permanently open for gas exchange.

A particularly compact construction and a particularly simple design of the sterile barrier are obtained when the first carrier and the second carrier are arranged parallel or substantially parallel to one another.

A first gas flow cross section of the sterile flow path, which is sufficient for gas exchange, is ensured when in the sterile position a spacing of the one carrier from the ring-shaped projections of the other carrier is smaller than a height of the ring-shaped projections of the one carrier.

In order that a large air mass exchange can be ensured between the outside environment and the interior of the sterile container, it is advantageous for a spacing of the one carrier from the ring-shaped projections of the other carrier to be greater than a height of the ring-shaped projections of the one carrier in the overpressure position.

To reduce the number of movable parts, it is advantageous for one of the two carriers to be immovably connected to the sterile container.

A connection which may prove susceptible to failure can be dispensed with when one of the two carriers is formed integrally with the sterile container.

To establish a fluid connection with the environment outside of the sterile container, it is advantageous for one of the two carriers to have a gas exchange opening which is in fluid communication with the environment outside of the sterile container, and for the ring-shaped projections of one of the two carriers to concentrically surround the gas exchange opening. In particular, it is then only necessary for a single opening to be provided on the sterile container, and this may be surrounded by structures of one part of the sterile barrier. This additionally simplifies the design of the sterile container and the sterile barrier.

In order to enlarge a gas flow cross section of the sterile flow path in a particularly simple way, it is advantageous for the second carrier to be mounted on the sterile container so as to be movable relative to the first carrier. With this configuration, an alteration in the gas flow cross section of the sterile flow path is achieved by the two carriers being moved relative to one another.

Advantageously, at least one stop is provided for specifying a minimum spacing between the first carrier and the second carrier. This prevents the two carriers from approaching one another so far that a sterile flow path is completely closed, which, in principle, is not, but, in exceptional cases, may be desired. Normally, however, the sterile flow path is intended to be permanently open so as to allow permanent gas exchange between the environment outside of the sterile container and the receiving space therein.

In principle, it would be conceivable for the first carrier to carry the at least one stop. It is, however, particularly advantageous for the second carrier to carry the at least one stop. In particular, when the movably mounted carrier carries the at least one stop, the stop can then be used for both guaranteeing a spacing between the two carriers and centering these relative to one another, which is particularly advantageous in the case of a sterile barrier in the form of a Pasteurian loop (tortuous path).

The design of the sterile barrier becomes particularly simple when the at least one stop is constructed in the form of a projection, and when a height of the projection corresponds to the minimum spacing between the first carrier and the second carrier. One of the two carriers may, therefore, come to rest directly on the stop.

A sterile container becomes particularly simple to manufacture when the sterile barrier and/or the gas exchange opening are of substantially circular design.

In order to hold the sterile barrier or at least one part thereof in a simple way on the sterile container, it may be advantageous for the holding device to comprise at least one holding element for holding and/or supporting at least one part of the sterile barrier.

In accordance with a preferred embodiment of the invention, it may be provided that the at least one holding element is mounted so as to be movable on the sterile container. In particular, this allows at least one part of the sterile barrier to be immovably connected to a holding element, so that the at least one part of the sterile barrier is then still mounted so as to be movable relative to the sterile container.

It is advantageous for the at least one holding element to be held in a biased manner on the sterile container, so that when a pressure difference is smaller than the minimum pressure difference, the sterile container will assume the sterile position. It is thereby ensured that the overpressure flow path will only be opened when it is really required, namely when the minimum pressure difference is exceeded.

In accordance with a further preferred embodiment of the invention, it may be provided that the sterile barrier comprises at least one holding portion, that the holding device comprises at least one holding element, and that the at least one holding portion is supported on the at least one holding element. Thus, the sterile barrier or a part thereof can be held in a defined manner on the sterile container, in particular, connected thereto or movably mounted thereon.

A particularly simple holding is made possible by the at least one holding element comprising a holding arm which covers the holding portion and is arranged so as to extend parallel or substantially parallel to a sterile container wall carrying the sterile barrier. For example, the holding portion can be held clamped against a wall of the sterile container by the holding arm in the closed position.

The at least one holding element advantageously extends over an angular range in the circumferential direction of the sterile barrier. The sterile barrier or a part thereof is thereby prevented from being able to move in an undesired manner relative to the sterile container, in particular, parallel to a wall thereof. The at least one holding element thus also serves as a kind of centering device.

It is advantageous for the angular range to have values of from 100° to 50°, in particular, 20°, so as to be able to use a plurality of holding elements that are as small as possible.

In principle, it would be possible to provide a single holding element. However, a particularly secure holding of the sterile barrier on the sterile container is ensured when at least two holding elements are provided, and when the at least two holding elements are arranged symmetrically around the sterile barrier. In particular, it is advantageous for four holding elements to be arranged symmetrically around the sterile barrier.

In principle, it would be possible to arrange the sterile barrier on a container wall or on the container bottom. It is, however, particularly easily accessed, in particular, for cleaning purposes, when it is arranged on the lid.

In order that the sterile barrier and the objects accommodated in the receiving space will not be destroyed when the overpressure flow path is opened abruptly, for example, due to unintentional release of a part of the sterile barrier from a holding device holding it, it may be advantageous for at least one stop to be provided for delimiting a maximum gas flow cross section of the sterile flow path.

The sterile container is particularly light and easy to manufacture when the lid and/or the sterile barrier is/are made from a plastic material, in particular, from polyetheretherketone (PEEK) or polyphenylene sulfone (PPSU). It would also be conceivable to additionally reinforce the plastic material, for example, with glass fibers and/or carbon fibers.

It is advantageous when in the overpressure position the pressure prevailing in the environment outside of the sterile container exceeds the pressure prevailing in the receiving space by at least the minimum pressure difference. This means that the overpressure flow path is at least partially open when in the environment outside of the sterile container a pressure prevails, which is greater than the pressure prevailing in the receiving space by at least the minimum pressure difference. Accordingly, a pressure difference prevailing, for example, during sterilization of the sterile container can be reduced by at least partially opening the overpressure flow path and thereby allowing hot steam to flow into the receiving space. The variable flow cross section thus makes it possible for a kind of pressure relief valve to be created in the form of an inlet valve.

The following description of a preferred embodiment of the invention serves to explain the invention in greater detail in conjunction with the drawings.

DETAILED DESCRIPTION OF THE INVENTION

Figure 1:
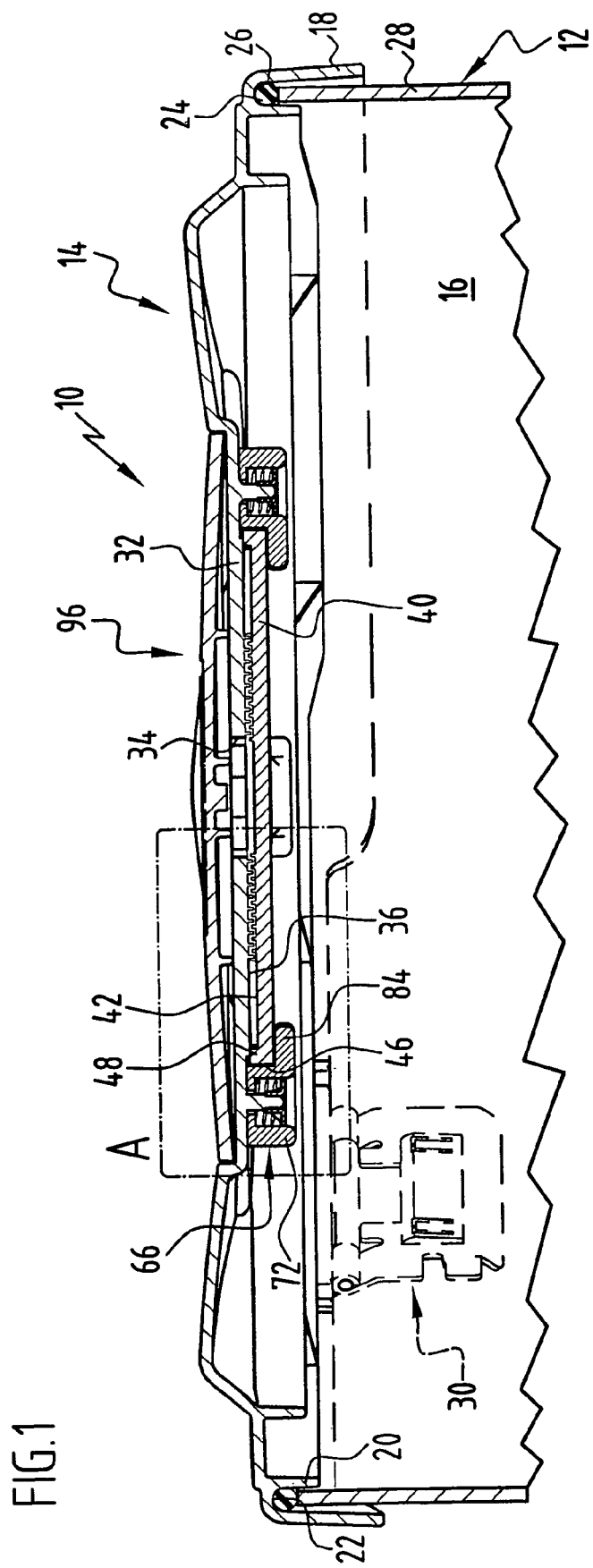
FIG. 1: a partly sectional view through a sterile container.

FIG. 1 shows a sterile container, generally designated by reference numeral 10, which comprises a container tray 12 and a lid 14 for closing the container tray 12. Surgical instruments and surgical material may, for example, be stored in an interior 16 of the sterile container 10.

The lid 14 has a vertically projecting, circumferential rim 18 and a somewhat shorter projection 20 extending parallel thereto. The rim 18 and the projection 20 define between them a circumferential sealing groove 22 in which a seal 24 is inserted. The sealing groove 22 serves to receive front edges 26 of walls 28 of the container tray 12. The seal 24 comes to rest directly on the front edges 26 and is compressed somewhat by two closure latches 30 arranged opposite one another on the lid 14, when locking the container tray 12, so that the lid 14 closes the container tray 12 in a gas-tight manner.

A circular inlet opening 34 is provided in a lid wall 32 at the center of the lid 14 and is surrounded by concentric ring projections 38 extending vertically from an inner surface 36 of the lid wall 32. The lid wall 32 thus forms a first carrier for the ring projections 38. A carrier plate 40 in the form of a flat disc forms a second carrier. Concentric, ring-shaped projections 44 extend from a side surface 42, facing the inner surface 36, of the carrier plate 40. Their wall thickness is smaller than a spacing between adjacent projections 44. A wall thickness of the ring projections 38 is likewise smaller than a spacing between two adjacent ring projections 38.

The radii of the ring projections 38 and the projections 44 are selected so that both the ring projections 38 and the projections 44 are aligned concentrically, with a ring projection 38 entering partially between two projections 44 and a projection 44 between two ring projections 38, respectively.

Furthermore, four spacers 48 are arranged on the side surface 42 adjacent a side edge 46 of the carrier plate 40 so as to project from the side surface 42. The spacers 48 are distributed uniformly over the circumference of the carrier plate 40 and each extend over an angular range 50 of approximately 20°. A height of the spacers 48, starting from the side surface 42, is both greater than a height 52 of the ring projections 38, starting from the inner surface 36, and greater than a height 56 of the projections 44, starting from the side surface 42.

Figure 2:
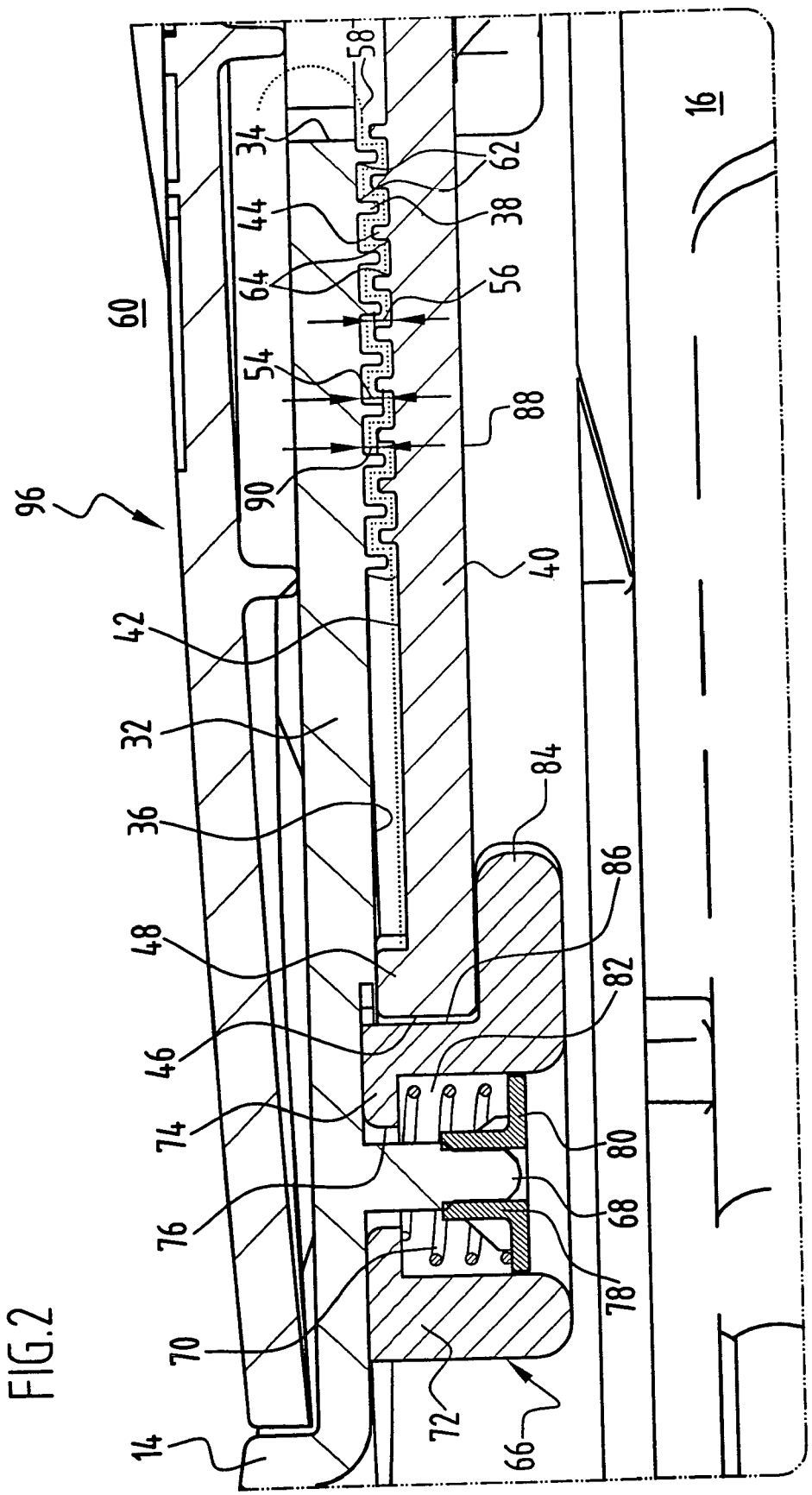
FIG. 2: an enlarged view of area A in FIG. 1 with a sterile barrier in the sterile position.

The spacers 48, which bear against the inner surface 36, define a minimum spacing of the inner surface 36 from the side surface 42. In this sterile position, shown in FIGS. 1 and 2, a meander-shaped flow path 58, indicated by a dotted line in FIG. 2, is thus formed. It connects the interior 16 of the sterile container 10 with an environment 60 outside thereof. The meander-shaped flow path 58 is also referred to as Pasteurian loop (tortuous path) and exhibits a special effect, namely that particles carried along in a flow of gas flowing along the flow path 58, for example, germs and bacteria, collect in corners 62 in the area of transition between the ring projections 38 and the inner surface 36 and in corners 64 in the area of transition between the projections 44 and the side surface 42 due to the absence of a flow in the aforementioned areas. Owing to the large number of windings in the flow path 58 and, consequently, the large number of flow-free areas, particles carried along in the flow of gas are, so to speak, filtered out by deposition in the corners 62 and 64.

The carrier plate 40 is mounted by means of four identical holding devices 66 so as to be movable on the lid wall 32. Each of the holding devices 66 has a bearing pin 68 projecting perpendicularly from the inner surface 36. The bearing pin 68 is surrounded by a pot-shaped bearing element 72 having a bottom 74 bearing against the inner surface 36. The bottom 74 has, in turn, a bore 76 which is somewhat larger in diameter than a diameter of the bearing pin 68. A terminating sleeve with a radially projecting ring flange 80 is positioned on the bearing pin 68. The diameter of the ring flange 80 corresponds approximately to an inner diameter of the bearing element 72. In this way, a ring space 82 surrounding the bearing pin 68 is delimited by the ring flange 80 of the terminating sleeve 78 and by the bearing element 72. Inserted in the ring space 82 is a helical spring 70 which is supported, on the one hand, on the ring flange 80 and, on the other hand, on the bottom 74 of the bearing element 72. Owing to this special arrangement, the bearing element 72 is biased by the helical spring 70 in a normal position corresponding to the sterile position against the inner surface 36.

A bearing projection 84 extends transversely, i. e., parallel to the inner surface 36, from the bearing element 72, so that the bearing element 72 forms together with the inner surface 36 a groove-shaped receptacle 86 for mounting the carrier plate 40. The bearing projection 84 bears against an underside 88 of the carrier plate 40. Owing to the action of the helical spring 70, the bearing projection 84 is pressed against the underside 88, so that the carrier plate 40 bears with the spacers 48 against the inner surface 36 in the normal position.

Figure 3:
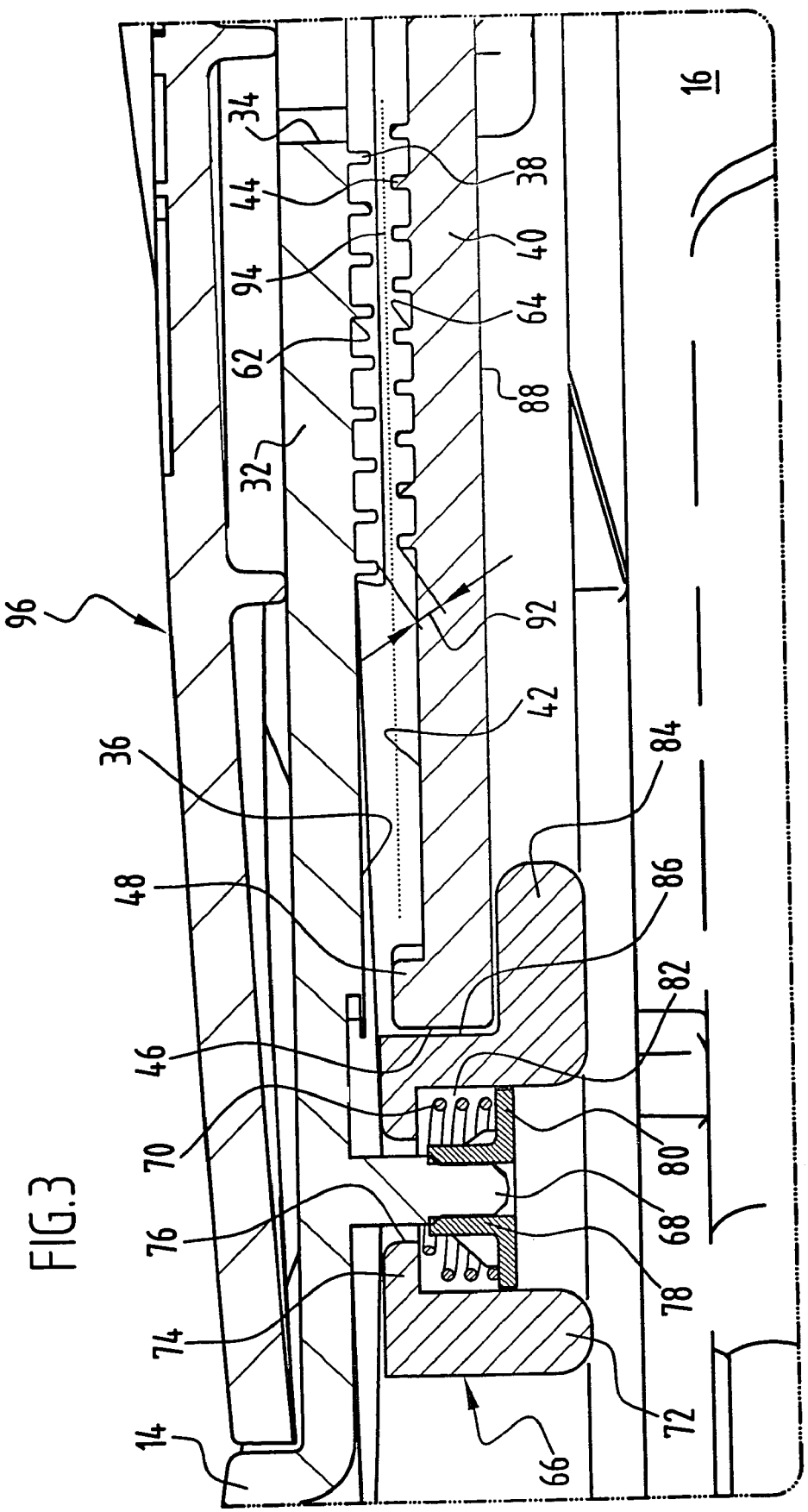
FIG. 3: a view similar to FIG. 2 with the sterile barrier in the overpressure position.
Figure 4:
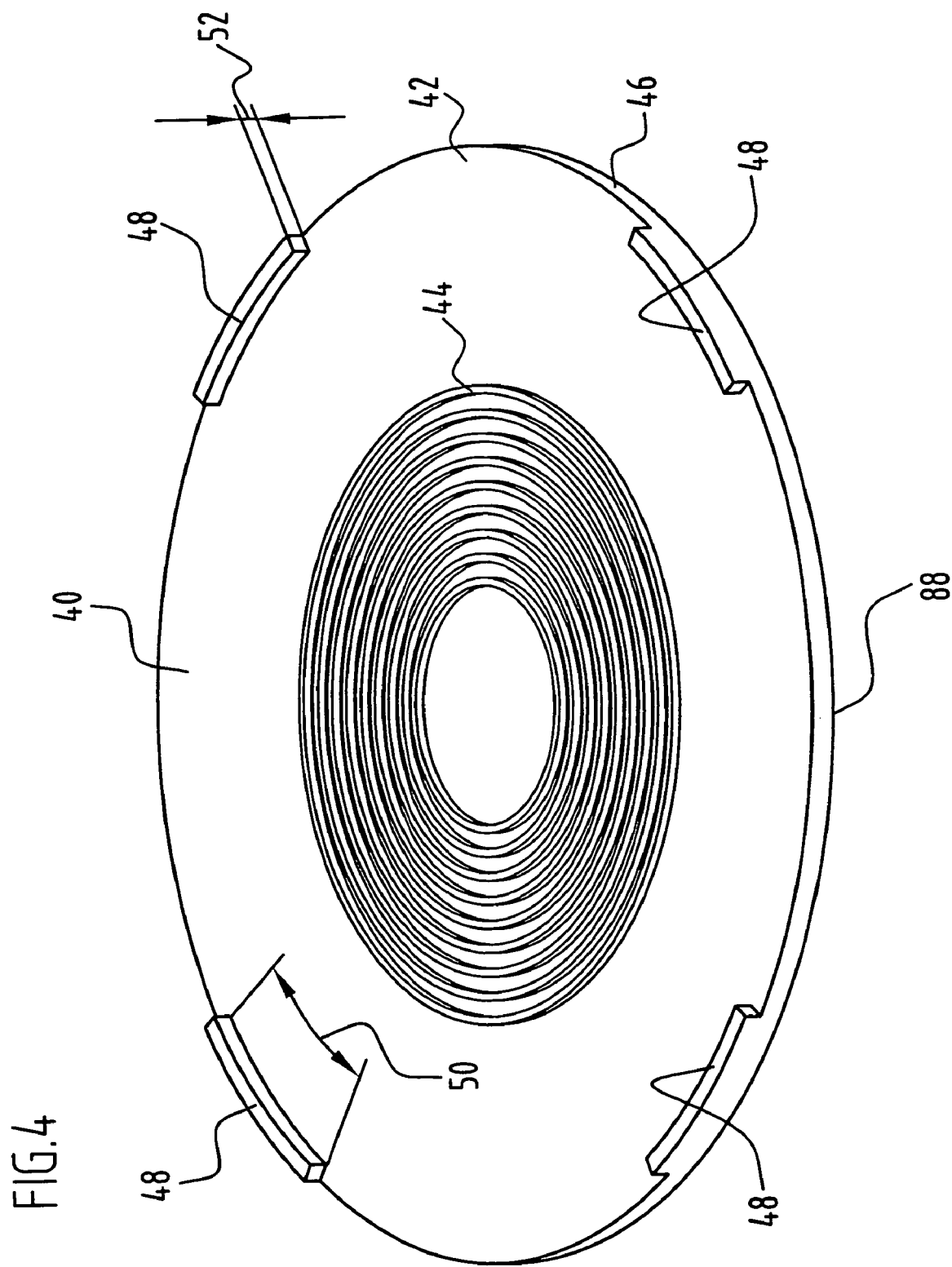
FIG. 4: a perspective view of a movably mounted part of the sterile barrier.

In the normal or sterile position shown in FIG. 2, the flow path 58 has a cross section designated 90. When the pressure in the environment 60 outside of the sterile container 10 rises in relation to a pressure in the interior 16, the carrier plate 40 is pressed against the bearing projections 84, and the bottom of the bearing element 72 thereby compresses the helical spring 70 supported on the ring flange 80. This causes a spacing between the side surface 42 and the inner surface 36 to be increased, with the result that the flow path 58 has a cross section 92, which is larger than the cross section 90. Owing to the increase in the cross section 90 of the flow path 58, a straight-lined flow path 94 is formed between the ring projections 38 and the projections 44, by means of which the excessive pressure difference can be reduced. The flow path 94 thus forms an overpressure flow path. In this overpressure position shown in FIG. 3, the effect of the Pasteurian loop (tortuous path) owing to the meander-shaped flow path 58 is shut off. When the pressure acting on the carrier plate 40 drops again, the helical springs 70 press the bearing elements 72 against the inner surface 36 again, so that the sterile barrier formed by the carrier plate 40 together with the ring projections 38 and the projections 44 is transferred again to the sterile position shown in FIG. 2.

All of the elements of the lid are preferably made from a plastic material, so that corrosion of the lid 14 is minimized.

On an outer side of the lid 14, a protective cover 96 is clipped in a manner not shown in greater detail onto the lid 14 so as to completely cover the inlet opening 34.

The invention claimed is:

1. Sterile container for receiving and storing surgical instruments or surgical material under sterile conditions, comprising:
    a receiving space formed by a container bottom and container walls,
    a lid for closing the receiving space,
    a sterile barrier defining a single flow path establishing a single fluid connection between the receiving space and an environment outside of the sterile container, the flow path comprising a sterile flow path when the sterile container is in a sterile position and an overpressure flow path when the sterile container is in an overpressure position, a gas flow cross section of the sterile flow path being alterable for formation of the overpressure flow path, the single fluid connection being common to the sterile flow path and the overpressure flow path;
    wherein:
    the overpressure flow path is closed when the sterile container is in the sterile position in which an exchange of gas between the receiving space and the environment outside of the sterile container is only possible through the sterile flow path, and
    the overpressure flow path is at least partially open when the sterile container is in the overpressure position in which a pressure difference between pressures prevailing in the receiving space and in the environment outside of the sterile container exceeds a minimum pressure difference.

2. Sterile container in accordance with claim 1, wherein in the sterile position the sterile flow path has a first flow cross section, in the overpressure position the sterile flow path has a second flow cross section, and the overpressure flow path has a third flow cross section, which corresponds to the difference between the first flow cross section and the second flow cross section.

3. Sterile container in accordance with claim 1, wherein the sterile barrier is arranged on an inner side of the sterile container.

4. Sterile container in accordance with claim 1, wherein a holding device is provided for holding at least one part of the sterile barrier on the sterile container.

5. Sterile container in accordance with claim 4, wherein the at least one part of the sterile barrier and the holding device are releasably connectable, and the at least one part of the sterile barrier is releasable from the holding device in a remove position and is held on the holding device in a connect position.

6. Sterile container in accordance with claim 4, wherein the holding device comprises at least one holding element for holding and/or supporting at least one part of the sterile barrier.

7. Sterile container in accordance with claim 6, wherein the at least one holding element is mounted so as to be movable on the sterile container.

8. Sterile container in accordance with claim 6, wherein the at least one holding element is held in a biased manner on the sterile container, so that the sterile container will assume the sterile position when a pressure difference is smaller than the minimum pressure difference.

9. Sterile container in accordance with claim 6, wherein the sterile barrier comprises at least one holding portion, the holding device comprises at least one holding element, and the at least one holding portion is supported on the at least one holding element.

10. Sterile container in accordance with claim 9, wherein the at least one holding element comprises a holding arm which covers the holding portion and is arranged so as to extend parallel or substantially parallel to a wall of the sterile container, which carries the sterile barrier.

11. Sterile container in accordance with claim 6, wherein the at least one holding element extends over an angular range in a circumferential direction of the sterile barrier.

12. Sterile container in accordance with claim 11, wherein values of the angular range are from 10° to 50°, in particular, 20°.

13. Sterile container in accordance with claim 6, wherein at least two holding elements are provided, and the at least two holding elements are arranged symmetrically around the sterile barrier.

14. Sterile container in accordance with claim 1, wherein the sterile barrier is constructed in the form of a Pasteurian loop (tortuous path), and the sterile flow path is of meander-shaped configuration.

15. Sterile container in accordance with claim 14, wherein the Pasteurian loop (tortuous path) comprises a first carrier and a second carrier facing the first carrier, the first and second carriers each carry concentric ring-shaped projections which extend in a direction towards the respective other carrier, and in the sterile position a ring-shaped projection of one carrier respectively enters at least partially in between two ring-shaped projections of the other carrier.

16. Sterile container in accordance with claim 15, wherein the ring-shaped projections of the one carrier have a wall thickness which is smaller than a spacing between adjacent ring-shaped projections of the other carrier.

17. Sterile container in accordance with claim 15, wherein the ring-shaped projections of the two carriers have a height which is smaller than a spacing of the two carriers from one another in the sterile position.

18. Sterile container in accordance with claim 15, wherein the first carrier and the second carrier are arranged parallel or substantially parallel to one another.

19. Sterile container in accordance with claim 15, wherein in the sterile position a vertical spacing of the one carrier from the ring-shaped projections of the other carrier is smaller than a height of the ring-shaped projections of the one carrier.

20. Sterile container in accordance with claim 15, wherein in the overpressure position a vertical spacing of the one carrier from the ring-shaped projections of the other carrier is greater than a height of the ring-shaped projections of the one carrier.

21. Sterile container in accordance with claim 15, wherein one of the two carriers is immovably connected to the sterile container.

22. Sterile container in accordance with claim 21, wherein one of the two carriers is formed integrally with the sterile container.

23. Sterile container in accordance with claim 15, wherein:
the single fluid connection comprises a gas exchange opening,
the gas exchange opening is provided on one of the two carriers and
the ring-shaped projections of one of the two carriers concentrically surround the gas exchange opening.

24. Sterile container in accordance with claim 15, wherein the second carrier is mounted on the sterile container so as to be movable relative to the first carrier.

25. Sterile container in accordance with claim 15, wherein at least one stop is provided for specifying a minimum spacing between the first and the second carriers.

26. Sterile container in accordance with claim 25, wherein the second carrier carries the at least one stop.

27. Sterile container in accordance with claim 25, wherein the at least one stop is constructed in the form of a projection, and a height of the projection corresponds to the minimum spacing between the first and the second carriers.

28. Sterile container in accordance with claim 1, wherein:
the single fluid connection comprises a gas exchange opening, and
the sterile barrier and/or the gas exchange opening is/are of circular or substantially circular construction.

29. Sterile container in accordance with claim 1, wherein the sterile barrier is arranged on the lid.

30. Sterile container in accordance with claim 1, wherein at least one stop is provided for delimiting a maximum gas flow cross section of the sterile flow path.

31. Sterile container in accordance with claim 1, wherein the lid and/or the sterile barrier is/are made from a plastic material, in particular, from polyetheretherketone (PEEK) or polyphenylene sulfone (PPSU).

32. Sterile container in accordance with claim 1, wherein in the overpressure position the pressure prevailing in the environment outside of the sterile container exceeds the pressure prevailing in the receiving space by at least the minimum pressure difference.

* * * * *